US005533401A

United States Patent [19]
Gilmore

[11] Patent Number: 5,533,401
[45] Date of Patent: Jul. 9, 1996

[54] MULTIZONE ULTRASONIC INSPECTION METHOD AND APPARATUS

[75] Inventor: Robert S. Gilmore, Burnt Hills, N.Y.

[73] Assignee: General Electric Company, Schenectady, N.Y.

[21] Appl. No.: 241,520

[22] Filed: May 12, 1994

[51] Int. Cl.$^6$ ........................... G01N 29/10; G01N 29/26
[52] U.S. Cl. ................. 73/622; 73/620; 73/625; 73/628; 73/641
[58] Field of Search ............................. 73/642, 644, 622, 73/620, 628, 625, 626, 618, 627, 641, 637

[56] References Cited

U.S. PATENT DOCUMENTS

| | | | |
|---|---|---|---|
| 3,815,409 | 6/1974 | Macovski | 73/642 |
| 3,898,840 | 8/1975 | McElroy | 73/644 |
| 3,924,454 | 12/1975 | McElroy et al. | 73/628 |
| 3,942,361 | 3/1976 | Rath et al. | 73/626 |
| 4,075,883 | 2/1978 | Glover | 73/618 |
| 4,121,468 | 10/1978 | Glover et al. | 73/622 |
| 4,523,468 | 6/1985 | Derkacs et al. | 73/622 |
| 4,641,532 | 2/1987 | Rohrer | 73/622 |
| 4,821,574 | 4/1989 | Takamizawa | 73/602 |
| 5,108,693 | 4/1992 | Landry et al. | 73/637 |
| 5,179,954 | 1/1993 | Arima et al. | 73/621 |

*Primary Examiner*—Hezron E. Williams
*Assistant Examiner*—Nashmiya Ashraf
*Attorney, Agent, or Firm*—David C. Goldman; Marvin Snyder

[57] ABSTRACT

A multizone ultrasonic inspection apparatus and method of employing the apparatus for inspecting titanium billets is provided, in which a plurality of ultrasonic transducers having focal zones of increasing depth are positioned to examine a cylindrical billet of titanium through the thickness of the billet. The focal zones partially overlap the adjacent focal zones, thus assuring complete examination through the thickness of the entire billet. The reflected signals from the transducer receivers are processed into digital form in order to be used in generating an image of the billet undergoing inspection, and to be used in storing the image data in, for example, a hard disk or an optical disk.

15 Claims, 3 Drawing Sheets fig. 1 fig. 2 fig. 3

MULTIZONE ULTRASONIC INSPECTION METHOD AND APPARATUS

BACKGROUND OF THE INVENTION

1. Field of the Invention

This invention relates to an ultrasonic inspection system for use in non-destructive testing of titanium and other materials in cylindrical billet form, in which a plurality of transducers are employed to take readings at varying depths through the thickness of the billet.

2. Description of Related Art

In order to assure that only the highest quality titanium is die-forged into aircraft engine disks, the material must be inspected in the billet stage to the best possible sensitivity. Because the billets are hot worked, most of the porosity and shrink present in the cast ingots have been closed and healed. While some porosity can survive the billet process, these pores will probably be healed by the die forging of the disk blanks. Therefore the flaws of primary concern are inclusions, one type of which is a nitrogen stabilized "hard alpha" phase found in titanium. Other undesirable inclusions are oxides and silicates. Other types of flaws, such as voids, are also of concern.

Ultrasonic inspection is employed to attempt to detect all flaws in the materials which would be detrimental to the performance of the material as an aircraft engine spool or disk, especially the aforenoted "hard alpha" inclusions. One difficulty previously experienced in using ultrasonic testing has been in obtaining reliable readings through the entire thickness of the material under test, and in pinpointing the location of the flaws detected.

In the beginning stages of the overall process of die forging titanium aircraft disks, a titanium billet is formed from a cropped cylindrical ingot usually about 30–36 inches in diameter and 7000–10,000 pounds in weight. The ingot is rotary forged into a series of cylindrical billets. These can vary from 6 to 15 inches in diameter. Billets that are six inches in diameter will weigh 55 pounds per foot of length, a billet with a 12-inch diameter will weigh 218 pounds per foot, and 15" diameter billets will weigh 340 pounds per foot. The individual billet segments are seldom less than 10 feet long, and seldom exceed 20 feet in length.

When rotary scanners are used to scan the billets, the maximum inspection depth is equal to the billet radius, or from 3.0" to 6.5" for a 6–13" range in billet diameter. In order to produce uniform test sensitivities, current ultrasonic inspection systems use distance compensated gain (DCG) amplifiers that increase gain as the distance from the transducer increases. This strategy ignores the decrease in acoustic signal to noise (S/N) ratio produced by beam spread. Because acoustic noise is also amplified with system gain, and titanium has high acoustic noise, DCG combined with beam spread results in low flaw S/N ratios, particularly at the billet centerlines. Since the primary factor limiting detection is acoustic noise, the use of DCG techniques produces no improvement in flaw S/N or in the probability of detection (POD) for flaws.

Current ultrasonic systems scan billets with small (1"×½") cylindrically focused transducers. These small sizes produce diffraction limited near field limits (foci) at depths of less than 2.0" in the billets rather than near the billet centerline. Therefore, all of the billet sizes insonified with these transducers have diverging beams at the centerline, which is the most likely region in which hard alpha flaws are present. Larger transducers have been used by some European manufacturers, such as the French titanium supplier CESUS, but three or fewer such transducers are used in the inspection process, and careful attention has not been given to the uniformity of the beam overlap.

The current ultrasonic inspection systems (including those used by CESUS) do not produce uniform ultrasonic interrogation of the billet interior. Quasi-uniform test sensitivity is produced by DCG amplifiers. This does amplify the weaker signals resulting from deeper reflectors and therefore permits the use of a single amplitude threshold at all depths. However, as discussed above, DCG amplifiers operate on both the flaw signal and the noise and therefore do not improve flaw detection.

Recently, several phased array systems have been evaluated for billet testing. The phased array generally involves transmitting a large number of ultrasonic pulses into the material, with the numerous pulses focused at different depths. The most serious limitation in the use of phased array transducer systems for testing large material volumes is the high pulse repetition rates required for the single phased array transmitter to transmit the multiple focused beams at the number of billet depths necessary to obtain the desired flaw detection capabilities. In thick material sections, high repetition rates always result in unattenuated sound and these remnant pulses result in a high number of false flaw detections. In order to reduce the repetition rate, low scanning rates must be used, resulting in long inspection times. The trade-offs between long inspection times, high false calls and the current high cost of multiple channel phased array systems make phased arrays impractical for titanium billet testing.

In an initial attempt to overcome these disadvantages, a multiple transducer inspection system was developed in which a linear array of transducers focused at increasing, and overlapping, depths of focus was employed to insonify the billet as the billet was rotated in the immersion tank. The output of that system was in the form of a strip chart on which perturbations in the line tracings of the output of each transducer channel were used to locate potential flaws in the billet.

While representing a distinct improvement over then-existing inspection methods, this inspection method also evidenced several significant limitations. As an example, the strip chart provides no direct spatial correlation of the output to the billet itself. In order to partially overcome this limitation, the inspection apparatus was configured such that the strip chart output would be identical in length, i.e., up to 20 feet, to the billet being inspected. This enabled a physical comparison of the strip chart output to the billet, by overlapping the strip chart on the billet, wherein perturbations in the output could be traced at least to a specific axial location on the billet.

The strip chart output also was purely analog in form, as the chart was the only recording and/or storage medium, and no electronic storage of the output data was accomplished. Thus, there was no ability to view the results in any different form which might be of greater assistance in increasing the probability of flaw detection and in lowering the number of false flaw indications. The dynamic range of the strip chart output was also limited, and thus further limited the ability to accurately detect and pinpoint the location of flaws. In addition, it became apparent that the retention and archiving of the strip charts, which was the only form in which the data was recorded, would be extremely cumbersome.

SUMMARY OF THE INVENTION

The present invention overcomes the aforenoted limitations and disadvantages by employing a plurality of ultrasonic transducers having focal zones at increasing depths and with the adjacent focal zones overlapping each other, in combination with an advanced data acquisition apparatus which enables the billet to be imaged, for example, by producing a C-scan image from the output of the ultrasonic signals received by the transducers. The present invention further provides for electronic storage of the image data, and the imaging subassembly overcomes the other noted disadvantages of the strip chart output, namely, the dynamic range limitations and the inability to view the results in a different form.

The ultrasonic transducers are desirably linearly arranged and focused to different depths of the billet to be examined or inspected, beginning at the surface of the billet, and extending to at least the central axis of the billet. The transducers are designed such that, when used in conjunction with a cylindrical billet, each transducer will have a prolate spherical focal zone oriented transversely to the longitudinal axis of the cylinder. The focal zone of each of the transducers will partially overlap the focal zones of the transducers focused at the adjacent shallower and deeper depths. The plurality of transducers thus arranged provide the ability to inspect the entire volume of the billet as the billet is rotated and the transducers are moved longitudinally along a path parallel to the longitudinal axis of the billet.

The reflected echoes are received back by the transducers, and through positional data correlation and processing, a three-dimensional image is generated, in which representations of flaws such as hard-alpha inclusions can be viewed on a display, and can be stored in a desired magnetic memory device or other type of memory.

It is a principal object of the present invention to provide a nondestructive ultrasonic inspection method, and apparatus for performing the method, for efficiently inspecting an entire volume of a billet, generating an image of the billet using reflected ultrasonic energy, and displaying and/or storing the image in order to be able to locate flaws within the billet.

It is a further principal object of the present invention to provide a method, and an apparatus for performing the method, in which ultrasonic inspection of a plurality of overlapping zones extending from the surface of a billet to a central axis of the billet is achieved using transducers having varying and increasing depths of focus, and in which the transducers are translated along the longitudinal extent of the billet, thereby obtaining inspection of the entire thickness, while reducing the number of pulses necessary to complete the inspection, as compared with known phased array ultrasonic inspection systems and methods, with the results of the inspection being processed to produce an image of the billet which is displayed and/or stored.

BRIEF DESCRIPTION OF THE DRAWINGS

The above and other objects and advantages of the present invention will become apparent from a study of the following detailed description taken in conjunction with the accompanying drawings, in which like reference numerals refer to like elements throughout the several views, and in which.

DETAILED DESCRIPTION OF THE PREFERRED EMBODIMENT

Figure 1:
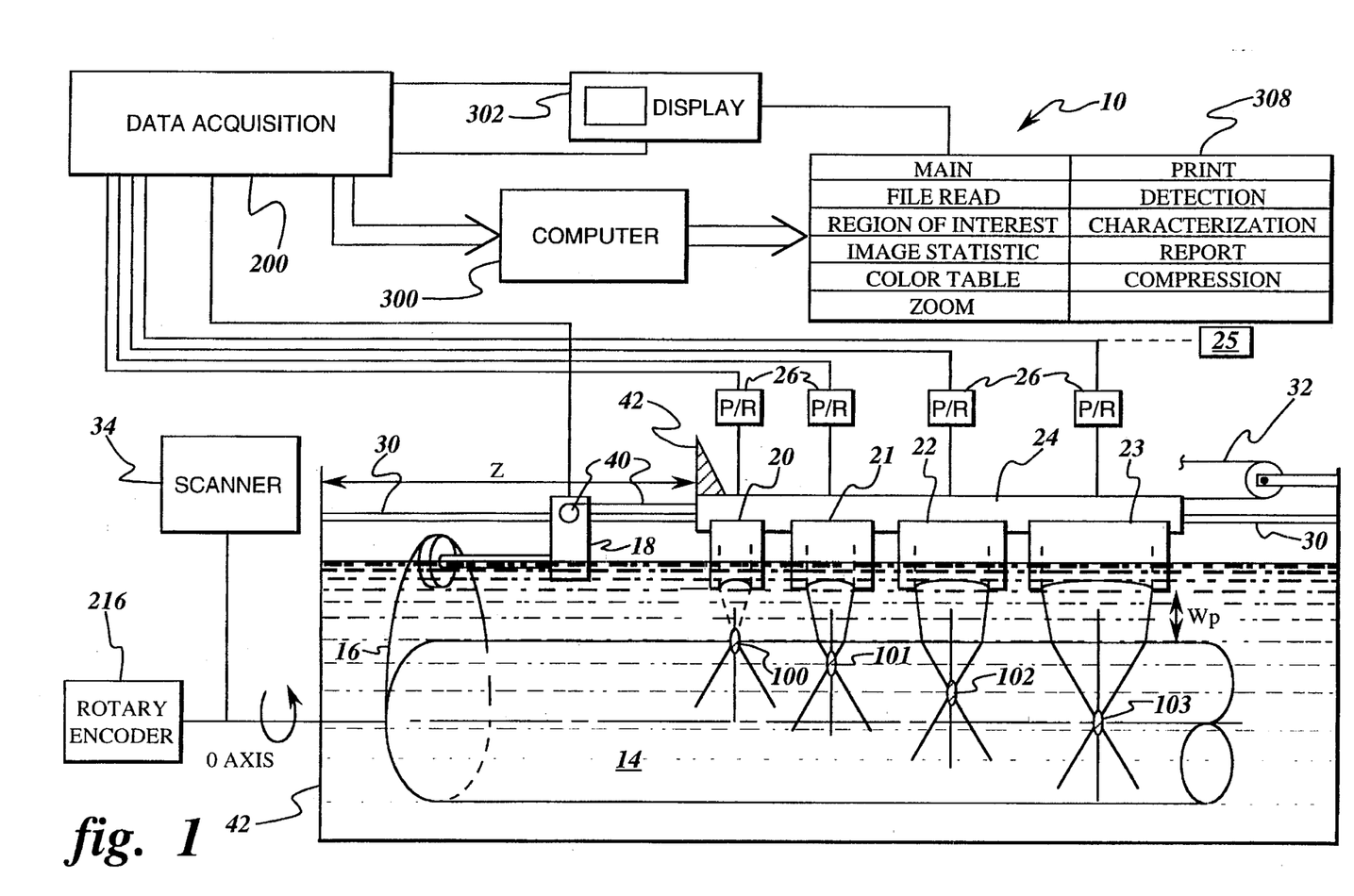
FIG. 1 depicts a substantially schematic view of the principal components of a multizone inspection system in accordance with a preferred embodiment of the present invention.

Referring initially to FIG. 1, a multizone inspection system according to the preferred embodiment of the present invention is designated generally at numeral 10. As noted previously, the multizone inspection system 10 has been designed primarily for use in inspecting cylindrical billets of metal, in particular, titanium billets which are ultimately fabricated into fan discs for jet engines. The system may, however, be used to non-destructively inspect any number of different kinds of objects for which an inspection of the complete volume is desired.

The multizone inspection system 10 is designed to be installed for use with conventional ultrasonic immersion handling equipment, which titanium billet manufacturers will generally already have installed at their production facilities. An immersion tank 12 is suitably sized to contain billets up to twenty (20) feet in length, twelve to fifteen (12–15) inches in diameter, and weighing between 4400–6800 pounds. A titanium billet 14 is conventionally immersed in water or other fluid in the tank 12 for the purposes of conducting the inspection.

A belt 16 and drive motor 18 (or similar drive device) are employed to engage and rotate the billet about its central longitudinal axis during the inspection process. For the purposes of conducting the inspection method in accordance with the present invention, the billet 14 is preferably rotated such that the surface speed at the outer surface is between about 6–12 inches per second, or 6–24 revolutions per minute.

The multizone inspection system replaces the known single transducer with a plurality of ultrasonic transducers spaced apart in an axial direction relative to the billet 14 disposed in the tank 12. Four such ultrasonic transducers 20, 21, 22, 23, are shown in FIG. 1 for the purposes of simplicity, but any number from three to eight transducers is considered to be the preferred range with the transducers in excess of four represented in block form at 25. Large diameter billets would generally dictate that a larger number of transducers be employed, in order to inspect the entire volume of the billet, as the total depth of inspection (the billet radius) will be greater for the larger billets. In applications in which it is contemplated that large diameter billets (up to 13", for example) will be inspected, eight transducers will generally be the preferred number. It will also be preferred to equip the inspection system with the number of transducers required to inspect the full radial depth of the largest anticipated billet, and to provide a control which would permit less than the entire set of transducers to be activated when billets of smaller radii are inspected.

The transducers 20–23 are preferably mounted on a transducer head 24 which maintains the transducers in fixed positions relative to one another in an axially spaced-apart manner, forming a linear array, as shown in FIG. 1. The nearest-neighbor spacing distances (distance between adjacent transducers) are preferably equal to the greatest inspection depth of the nearest neighbors, in order to eliminate cross-talk between the transducers. The transducers 20–23 alternatively could be spaced apart at the billet radius in a close-packed, staggered sequence.

Each of the plurality of transducers 20–23 is provided with a remote pulser/receiver 26, which transmits electrical energy to its associated transducer, causing the transducer to emit ultrasonic energy into the immersion fluid and the billet. Each pulser/receiver 26 also receives the electrical signal generated by its associated transducer when a reflected ultrasonic pulse is sensed by the transducer. This plurality of pulser/receivers 26 is in turn connected to the signal processing subsystem, which is described in greater detail later in the specification.

The transducer head 24 is mounted such that it can be translated in a longitudinal axial billet direction along the length of the billet. The head 24 may be slidably mounted on a track 30 and the means for effecting axial translation along what will be referred to as the z-axis, can be selected from a number of known devices, such as a rack and pinion drive or a belt drive shown schematically at 32, driven by a power take-off of the drive motor 18 used to rotate the billet. A scanner controller 34 operates the drive motor to sequence the billet through its rotations and to coordinate therewith the translation of the transducer head 24 through a series of inspection positions to acquire a C-Scan image of each inspection depth zone at each inspection position throughout the billet volume.

A rotary encoder 216 (see FIG. 2) is employed to keep track of the angular position of the billet being rotated, relative to a 0° set point selected at the beginning of the inspection cycle. The longitudinal position of the transducer head is similarly tracked by an axial position encoder.

The plurality of transducers 20–23 are shown schematically in FIG. 1 to have focal zones of increasing depths relative to the billet 14 undergoing inspection, extending from a focal zone 100 covering the outer surface of the billet 14 for transducer 20, to a focal zone 103 for transducer 23 covering the central longitudinal axis of the billet. It is an important aspect of this transducer arrangement to have each of the focal zones 100–103 partially overlap the adjacent focal zones in order to ensure that the entire volume of the billet is insonified and inspected. For example, the focal zones should be established such that a lower portion of focal zone 100 overlaps an upper portion of focal zone 101, i.e., the lower part of focal zone 100 reaches a depth which the upper part of focal zone 101 also includes. Each successive focal zone is similarly overlapped with the focal zones adjacent thereto. The combined set of focal zones 100–103 need only extend from the surface of the billet to the center of the billet in this embodiment, as the billet will be rotated during inspection such that the entire volume of the billet will be uniformly insonified at each axial data collection position.

It is desirable to mount the transducers having the increasing focal zone depths at the same distance from the billet undergoing inspection. Given that consideration, it will be readily understood that the transducers must have increasing diameters such that they can be focused at the increasing depths. The sizing and focusing of a transducer to inspect at a depth under a flat entry surface is an exercise well known in the art. This specific invention is particularly directed to the inspection of a cylindrical titanium billet being rotated in an immersion fluid such as water, and as such, the sizing and focusing of the transducers will preferably take into account the curvature of the billet entry surface.

The cylindrical curvature of the billet will cause the transducer beam to be defocused in the radial-circumferential plane. For plane wave incidence, the defocusing will be approximately equal to the water-titanium index of refraction, multiplied by the central angle intercepted by the ultrasonic beam at the billet surface. For the near surface inspection zones, the intercept angle will be small since a focused transducer beam will also be small and essentially the entry diameter will be little larger than the diffraction-limited beam diameter. A point-focused 5 Mhz, F/10 transducer, for instance, even when adjusted to inspect the first 1.2 inches of a 12" diameter Ti6-4 billet, would have a beam diameter at the billet surface of 0.24 inches. This would intercept a central angle of 2.3 degrees of arc. Since an F/10 beam converges at 2.86 degrees of arc, even at this shallow depth the beam is nearly defocused in the circumferential direction.

The effect of the cylindrical defocusing surface of the titanium billet is preferably compensated by over-focusing the convergent beam in the radial-circumferential plane of the billet. A transducer having a dual focus lens or a dual focus curved element, where the sharper lens or element curvature (for the cylindrical surface) is aligned perpendicularly to the longitudinal axis of the billet, can be provided. The technices used to design such lenses and transducers are described in R. S. Gilmore et al., "Reactive Focusing System for Ultrasonic Imaging", Rev. of Prog. in Quant. Nondestr. Eval., Vol. 7A (D. E. Chimenti and G. O. Thompson, Eds.), Plenum Press, New York, pp. 309–319 (1987), which is incorporated herein by reference. The lenses so described may be spherical (single radius of curvature), or aspheric (multiple radii of curvature). Single curvature lenses for the transducers have the benefit of providing a simpler transducer design, but the disadvantage of yielding a somewhat less accurate or sharp focus.

When a dual focus lens using two single radius curvatures is to be used, the object is to provide an annular curvature for the lens surface that will provide a point focus in the cylindrical billet. This can be accomplished by two ray-tracing calculations, one in the radial-axial plane of the billet, and a second in the radial circumferential plane. First, the desired focal zone size is selected and a convergent angle in the material required to produce this zone is calculated. Next the number of required inspection zones, or transducers, is determined by dividing the billet radius by the depth of focus and rounding off to the next highest integer (for an F/10 transducer and a 12" diameter billet, the calculation is 6.0/1.2=5). The inspection depths are assigned by placing the beam centers at the mid-depth of each of the inspection zones. The depths for an exemplary 12" diameter billet are 0.6, 1.8, 3.0, 4.2 and 5.4 inches, respectively. A water path (Wp) is then calculated. Finally, given values for the water path and other parameters employed in the ray-tracing calculations, the axial and circumferential curvatures for the wave front at Wp are calculated along with the two axial and circumferential diameters. If the transducer is to be fabricated with a dual focus lens and a flat element then the lens radii are calculated from the lens makers equation. The steps necessary to determine the design of an aspheric dual focus lens are much the same, but the calculations used yield a result which is used to operate machining equipment to fabricate the compound curvature for the lens.

Figure 2:
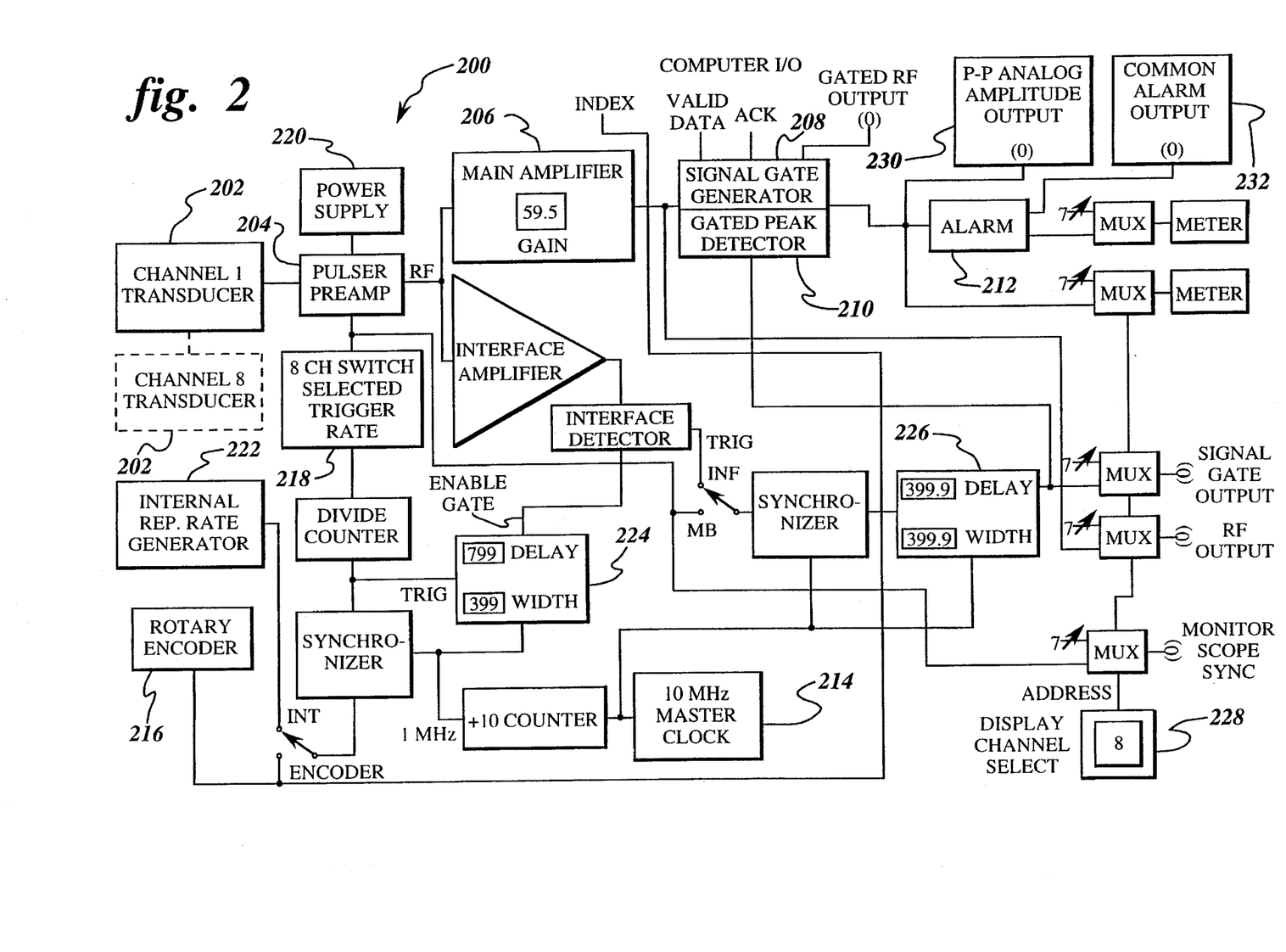
FIG. 2 is a block diagram of the data acquisition electronics for one transducer channel in accordance with a preferred embodiment of the present invention.

Turning now to FIG. 2, in the preferred embodiment of this invention, the data acquisition electronics package 200 for the ultrasonic multizone inspection system is depicted in block diagram form. The package 200 has a completely independent channel 202 for each transducer, each channel including a pulser/preamp 204, main amplifier 206, signal gate generator 208, gated peak detector (GPD) 210 and an alarm monitor 212 with adjustable threshold. It will be readily understood by those of ordinary skill in the art that FIG. 2 illustrates essentially only one channel, and that the components described above would be replicated for each additional channel of the plurality of transducers. All trigger signals are synchronized to an internal 10 Mhz master clock 214. The position and width of each signal gate and the amplifier gain are digital switch settable by the operator. The transducers are fired by a synchronized trigger from the rotary encoder 216 through a switch-selected binary division circuit. This selection allows substantially uniform acoustic beam inspection of each zone as the signal gates are positioned deeper into the material. The triggering rate of each channel can be individually selected by switch 218 or other suitable switching or selecting means.

The pulser/preamp 204 is in a box remote from its associated transducer, but mounted near the transducer. Since the near-zone (focused nearest the billet surface) transducer capacity is 175 pf and the deep-zone (focused nearest the billet center) capacity is 3500 pf, each pulser must be matched to its transducer for efficient operation at 5 MHz. The preamp is transformer coupled to the transducer for reduced input noise, has a 21 Mhz low pass filter and a gain of 14 dB. Each pulser/preamp is supplied with an isolated power supply 220. The trigger pulse, which fires each transducer, is derived from the internal repetition rate generator 222 or the rotary encoder 216 and synchronized to a 1 MHz clock and selected by the appropriate rate division. All transducers fire every 16th pulse, some fire every 8th pulse, some every 4th pulse and some every 2nd pulse of the maximum encoder rate (2048 pulses/revolution). Different channels can be fired at the same rate if that rate is selected for each transducer.

The synchronized rate trigger also starts a pair of 1 Mhz delay counter chips whose delay is set by digital switches and this generates an enabling gate for the constant fraction discriminator (CFD) 224. The delay range of the CFD enable gate is 799 microseconds and the width range is 399 microseconds. The interface signal is amplified and applied to the CFD which generates a start signal gate trigger from the interface signal within the CFD's enabling gate width. The water path distance is the same for all transducers so that one CFD enabling gate can be used for all 8 channels. The signal gate trigger can be selected from the CFD or from the main bang transducer trigger if the interface signal is weak or if shear wave inspection must be done. The signal gate trigger is resynchronized to the 10 MHz clock and applied to a pair of delay counters 226 which generate the signal gate of the gated peak detector 210. The signal gate delay range is 399.9 microseconds and width range is 399.9 microseconds.

The main amplifier 206 contains three cascaded 20 Db amplifiers, relays which switch in or out amplifiers every 20 Db, and a 5 pole Butterworth 23 MHz low pass filter. A digital switch controls the attenuator with 0.5 dB resolution and 0 dB attenuation is equal to a 60.6 dB amplifier gain. The equivalent input noise of the preamp plus amplifier at maximum gain (74 dB) is 8.3 microvolts RMS for 23 HMz bandwidth.

The gated peak detector 210 (GPD) is a simplified version of the GPD described in U.S. Pat. No. 4,620,444 entitled "High Speed Gated Peak Detector" issued to J. D. Young, and assigned to the assignee of the instant application. That patent is incorporated herein by reference. The signal gate closes an analog switch and opens the GPD clamp. The phase of the RF signal within the width of the selected gate is split into two positive peak detectors. The amplitude of each peak is sampled and held at the end of the signal gate. These two amplitudes are summed and held for the remaining repetition rate period, producing an analog voltage which is the peak-peak amplitude of the largest signal within the signal gate. The maximum analog output voltage is 10 volts and has a linear dynamic range of 40 dB. The GPD has an internal gain of 20 dB and a usable bandwidth of 10 MHz. The system's total gain is 94 dB.

Figure 3:
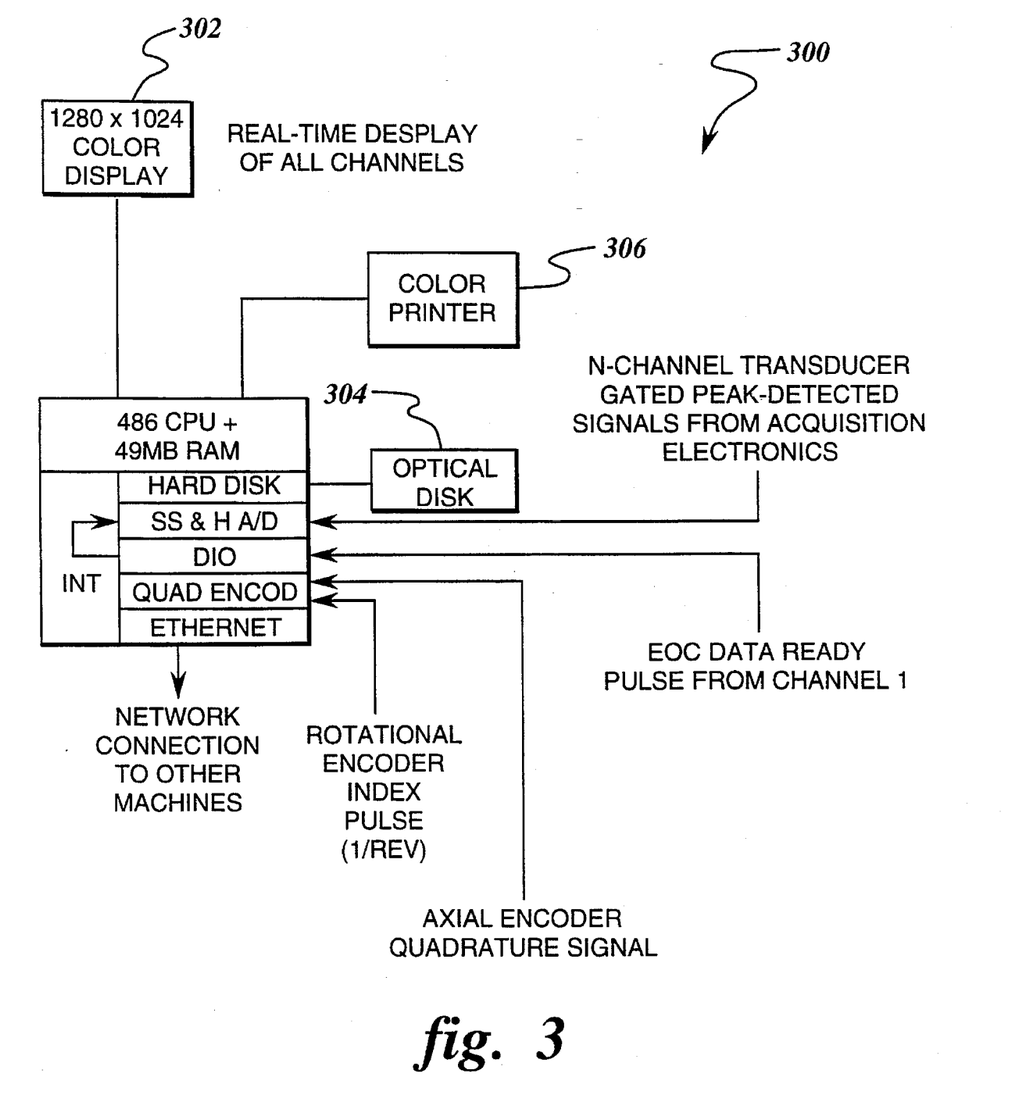
FIG. 3 is a block diagram of the computer system and selected peripheral components in accordance with a preferred embodiment of the present invention.

In the earlier work conducted related to a multizone inspection system, the GPD analog output voltage was displayed on an eight-channel strip chart recorder. Due to several aforenoted limitations with the strip chart recorded data, in accordance with the present invention, the GPD analog output voltage is preferably digitized to be used as imaging data by an 8 channel analog/digital converter card provided in a computer system 300 (FIGS. 1 and 3). In the preferred embodiment, Channel 1 has been designated the channel receiving the maximum trigger rate and provides the computer I/O hardware interrupt. The end of the signal gate sets a valid data line which the computer acknowledges by clearing the valid data signal. The index pulse from the rotary encoder 216 is used by the computer to start the data acquisition and to count the number of completed circumferential scan lines.

The alarm circuit 212 compares the GPD analog output level to an adjustable reference threshold level, triggers a flip-flop if the threshold is exceeded, lights a LED, and sets the common alarm output low. The operator notes which channel produced the alarm and can select the channel for display on a monitor or scope 302 (FIG. 1). The display channel select 228 provides the correct synchronization trigger to the monitor/scope 302, displays the selected channel's signal gate position and amplified RF waveforms, and continuously displays the peak-peak analog amplitude and alarm threshold level on LED digital voltmeters 230, 232, respectively, for the selected channel. The analog output voltmeter 230 is a convenient aid in the initial transducer alignment procedure and the gain setting for system calibration.

Turning again to FIG. 1 in combination with FIG. 3, the preferred computer system 300 used for data acquisition, imaging display, and storage is a personal computer having a 486/33 MHz CPU. In addition to the CPU, the computer system configuration preferably includes 49 MB of RAM on the motherboard, an 8-channel simultaneous sample and hold (SSH) ADC board, a digital I/O (DIO) board, an interrupt handler with a 1280×1024 resolution video board with 256 colors, 20" monitor 302, a quadrature encoder board, an ethernet card, high capacity hard drive, external SCSI 5.25" optical disk 304, and a color postscript printer 306.

The system is designed to acquire up to eight channels of analog ultrasonic image data from the acquisition electronics package 200, and display the image data in real-time. Images are also archived to optical disk 304 for permanent storage and hard copy can be obtained using the printer 306. If the PC is connected to the ethernet, images can be transferred to other machines with more power or tools for image processing. FIG. 3 shows a basic block diagram of the system 300.

In the billet inspection process, before image acquisition can begin, the user will generally be required to enter a number of parameters dealing with the material to be scanned. These can be entered as all new values or recalled from previously saved sets of parameters. The computer system 30 preferably gives the user instructions on how to set the acquisition electronics 200 for each channel based on billet diameter, number and characteristics of the transducers, and desired overlap between zones. The user will also generally be required to enter details about the specific billet being inspected, such as its length and identification numbers. Based on the billet length and number of transducers, the ADC is configured and an appropriate amount of RAM is allocated for the data from each channel. To put the system in acquisition mode, the user must press a start button. The computer system 300 will poll this input line until that pulse is seen at which time it will start taking data.

As described previously in the specification, the rotary encoder 216 drives the system. The computer system 300 uses the index pulse from the rotary encoder to start acquisition, to assure that the first sample received corresponds in the system to a zero degree point of the billet rotation.

Once in acquisition mode, the near channel (Channel 1) provides the hardware interrupt to the PC at the maximum receiving rate. This interrupt is fed into the DIO board in the PC. The interrupt handler in turn, triggers the ADC board. The reason for using this indirect technique is because, in this setup, only Channel 1 provides the data ready signal. Deeper channel signals will necessarily take longer to become valid because of physical propagation times of the ultrasonic pulse. To allow for this delay, a interrupt handler will be invoked by Channel 1 but will not trigger the ADC board until an amount of time equal to the delay of the deepest channel has passed.

The simultaneous sample and hold ADC can preferably be configured to read any number of channels e.g., (1–8) at setup, and during operation, it generally must sample all of these channels every time it is triggered. As a result, all lines from the electronics will be read every time even though some of the deeper channel signals may not be used for the smaller diameter billet inspections. The interrupt handler stores data using a double buffer scheme, each buffer holding one billet revolution of signals from all channels. At the completion of a revolution, the current acquisition buffer will be switched to the alternate buffer and the recently filled one can be processed and an image can be displayed.

The display of the data on monitor 302 involves showing all channel values at the same time. The screen resolution is preferably 1280 pixels wide by 1024 pixels high. In the preferred embodiment, commands and other static inspection information are displayed in an area 256 pixels wide by 1024 pixels high on the right side of the screen. The 1024 by 1024 area on the left of the screen is reserved for the real time data display. This square region is divided evenly into 8 horizontal "strips", each 128 pixels high. Each billet revolution results in the addition of one vertical line to each window corresponding to that transducer's received signal. For channels that contain more than 128 samples per revolution, the displayed signal is a compressed version where each pixel is the maximum of every (repetition rate)/128 data values. For a 1024 repetition rate channel, each display pixel would be the maximum of every 8 acquired data points. Since there would be an obvious loss of display resolution for compressed channels, a strip chart style display may be superimposed over the color C-scan data, which can aid in image interpretation. A line on the strip chart display shows the maximum raw value (ranging from 0–255) from each revolution plotted in a region of 128 pixels. This prevents high valued, "large area" signals, potentially containing important information concerning billet flaws, from going unnoticed due to the display compression algorithm.

When a full 1024 lines are displayed, the entire real-time display region is shifted one line to the left, discarding the oldest from the screen, and the newest line is drawn on the right side. Note that the "discarded" data is still safe in memory. Only the display is erased. In this manner, the illusion of a "sliding window" is given as the transducers 20–23 move down the billet 14.

To provide axial positional information for each line acquired, an axial encoder 40 with quadrature outputs is installed on the billet follower 42. These outputs are fed directly into a quadrature encoder card in the computer system 300. An index pulse from the rotary encoder 216 is used to latch the current quadrature counter value and this number is stored in an array. This records the exact location of the follower 42 and transducers 20–23 for each revolution or slice of ultrasonic data. Upon completion of the scan, the data from each channel is preferably saved in a separate file on a hard disk in the computer system 300, and then ultimately, for long term storage, off-loaded to SCSI optical disk drive 304. Along with the raw image data, a header containing information about the electronics and transducer setup for the channel and the array of axial encoder values are saved.

Viewer software allows the user to recall a particular data file and look at the configuration parameters in the header and the actual image data. The image may be viewed one window at a time with the window measuring 1024 pixels high by 1024 pixels wide. For images that contain less than 1024 samples per line, the image may be expanded vertically to fill the entire 1024 dimension. A printout can be obtained of the current image window on the attached color postscript printer.

Since the raw image data is composed of 8-bit values, it can also be read by other image processing software packages. There are a number of these products available which can run directly on the computer system 300 which is built out from a PC 486/33 MHz processor, or on a separate workstation. If the latter platform is chosen, an ethernet card installed in the computer system 300 provides the means for uploading the image files from the computer system.

An example of the data acquisition process of the present invention using the multizone transducer system is as follows. A 12" billet is scanned in five cylindrical shells, each 1.2" thick, with five 5 MHz, F/10 transducers. The transducers 20–23 transmit ultrasonic energy into the immersion fluid and into the billet in response to electrical pulses from pulser/receivers 26. The return or echo ultrasonic energy is received by the transducers 20–23, sending a return electrical pulse to pulser/receivers 26. The acquisition electronics package 200 controls this process using rotary encoder 216, and processes received electrical pulses, ultimately transmitting gated peak-detected signals to the computer system 300. The computer system 300 processes the signals and produces digital data which is then used to present images on the display or monitor 302 provided with the computer system. The data obtained from inspecting the 12"×240" billet would produce five large C-Scan images corresponding to hollow cylindrical regions of the billet at different depths of the billet. These images would represent the following zones of the billet:

| Zone | Size (in.) | Pixel Size (in.) | Approx. Image Size | |
|------|------------|------------------|--------------------|---|
| (1) | 37.7 × 240 | 0.04 | 1.00K × 6K | 6.0 MB |
| (2) | 30.2 × 240 | 0.04 | 0.75K × 6K | 4.5 |
| (3) | 22.6 × 240 | 0.04 | 0.50K × 6K | 3.0 |
| (4) | 15.1 × 240 | 0.04 | 0.38K × 6K | 2.4 |
| (5) | 7.6 × 240 | 0.04 | 0.20K × 6K | 1.2 |

| Zone | Size (in.) | Pixel Size (in.) | Approx. Image Size |
|---|---|---|---|
| Totals | | | 17.1 MB |

In accordance with the preferred embodiment of the present invention, the data for the zones indicated in the table above is preferably displayed in an imaging format. Multichannel Peak detector data (log or linear) provides an 8-bit per pixel image for each depth. The images could be taken at approximately equal pixel spacing for the O.D. surface of each zone by running a different divide by N for each zone sync rate.

Using a pixel size of 0.04", and taking images at approximately equal pixel spacing, rotating the billet at 20 RPM would provide 3 seconds per scan line, and would require 18K seconds (5.0 hours) to scan a 240" long billet. However, by increasing the pixel size to 0.06" the scan time can be reduced to 3.3 hours. Because all of the transducers fire simultaneously, the maximum pulse rate frequency, using the parameters of 0.04" pixels and 20 RPM billet rotation, is 333 Hz for the outer zones, i.e., well below the pulse rates that would cause unattenuated sound in the billet.

An image analysis portion 308 of the Multizone system consists of a set of software modules for performing various desired operations, which may be performed in any order on one or more previously-obtained Multizone image files. The modules will preferably be accessed through a graphical user interface (GUI) displayable on the monitor/display 302, and implemented on the system computer 300 using a commercial data analysis software package such as Interactive Data Language (IDL) by Research Systems Inc. (RSI) or PV-Wave by Visual Numerics. The coding of programs to perform the functions of these software modules, once the described functions or operations are understood, will be apparent to those skilled in the art.

The main module of the image analysis package 308 will preferably contain a graphics window for displaying a portion of a Multizone image. Since Multizone images tend to be large, this window will generally only display a portion of the image, but will have the ability to dynamically change the portion of the image which is currently being displayed in the graphics window (or scroll the image) such that the entire image may be viewed. The main module will also have the ability to display the value and location in pixel index, degrees or inches, of each data point in the image when that point is selected by the use of a pointing device (mouse). The main module also provides the ability to change the current zone being displayed in the graphics window. The zones may be accessed either sequentially or in a random order. Finally, the main module will provide access through the selection of different areas of the screen or buttons by the mouse to her modules which perform functions of interest. These modules will be described below. The main module will also provide logic functions to guide the user and prevent the selection of the modules in an improper order.

A file reading module allows the user to read in the data files from a given Billet ID and Heat Number, which are preferably used by the Multizone system to name data files. It also preferably provides the ability to search the system computer's file system to find file names which fall outside of the Multizone system convention.

A region of interest (ROI) module allows the user to define a rectangular region within the image currently in the graphics window for further analysis. Using this module a region of interest is designated by the user by marking the upper left and lower right hand corners of the region with the mouse.

An image statistics module allows the user to select, through the use of buttons and the mouse, a group of common statistics for the image amplitude values to compute and display, for either the whole image or an ROI if one has been defined. The group of statistics to display may include, but be not limited to, the following: extreme values and their location, value range, mean value, median value, and value standard deviation.

A color table module allows the user to interactively adjust the mapping from amplitude value to on-screen color which is commonly referred to as the color table. Choices will include both gray-scale and several pseudo-color tables. The user will also be able to adjust the contrast of the color table through the use of the mouse and an area of the screen known as a "slider".

A zoom module may preferably be provided, which will allow the user to display, at a larger size than the graphics window permits, a selected ROI. Zoom factors will include, but not be limited to, 1X, 2X and 4X.

A print module is further preferably provided, which will permit the user to send a full image or a ROI image to the system printer. The image will be printed in the current color table for the graphics window when the choice of system printer permits this. It will also contain, but not be limited to, appropriate labels such as the data file name and size/location of region printed, which may be generated automatically by the module or specified by the user.

A detection module is provided to allow the user to search the current set of multizone images for potential flaws. The Multizone inspection (as well as all other ultrasonic pulse-echo, C-scan inspections of large-grained metals) is plagued by grain noise which is ultrasonic reflections from grain interfaces. The grain noise may vary widely in a single billet, and has the potential to mask actual flaw indications or to produce false indications in defect-free regions. A novel method of dynamic thresholding for ultrasonic C-scan images can provide an improved detection process over traditional global thresholding when both probability of detection and false-alarm rate are considered. The dynamic thresholding method preferred for the present invention is a direct extension of the idea disclosed in U.S. patent application Ser. No. 08/118,337, filed Aug. 26, 1993, in the name of Howard and Gilmore. That application is assigned to the assignee of the present invention, and the disclosure of that application is hereby incorporated by reference herein. The extension of the method takes into account the potential correlation of grain noise between similar spatial locations in different zones. This additional correlation can be used to create a more accurate threshold. The method first divides the large images from one or more inspection zones into smaller subimages or regions. A threshold level is then computed from each of the regions based on a set of parameters derived from the region in question as well as adjacent regions. These regional threshold levels are converted into pixel threshold levels for the entire image using interpolation. In addition, the set of parameters upon which the regional threshold is based may be adjusted to fit the specific situation being addressed.

A characterization module allows the user to accurately characterize the size and shape of any of the flaws detected previously. The characterization of the flaws is done using two-dimensional Wiener filtering. This technique and its potential for characterizing flaws are described in K. W. Mitchell et al., "A True Weiner Filter Implementation for Improving Signal-to-Noise Resolution In Acoustic Images," Rev. of Prog. in Quant. Nondestr. Eval., Vol. II (E. E. Chementi and D. O. Thompson, Eds.), Planum Press, New York, pp. 895–902 (1992), the disclosure of which is hereby incorporated by reference. In brief, the filtering will reduce the blurring inherent in ultrasonic imaging systems to provide as accurate an estimate of flaw size as possible. Flaw size will be reported to the user as area, width, height, and percent of full screen height (FSH). A–6 Db of full screen height criterion will preferably be used in this module to define boundaries for size calculation.

A report module sends to the system printer a record of the data analysis performed on a given data set. This record may include, but not be limited to, the data file identification, image statistics, size and location of potential flaw indications, data acquisition settings, and user comments. This information may also be recorded in a data file independent of any image acquisition data file stored on the system computer's file system.

The compression module allows the user to compress or uncompress data files into system archive format. The compression scheme will preferably utilize a well-known image compression scheme such as Digital Pulse Code Modulation (DPCM).

While the preferred forms and embodiments of the invention have been illustrated and described herein, it will be apparent to those of ordinary skill in the art that various changes and modifications may be made without deviating from the inventive concepts and spirit of the invention as set forth above, and it is intended by the appended claims to define all such concepts which come within the full scope and true spirit of the invention.

What is claimed is:

1. A method for nondestructively examining an object having a longitudinal axis, the method comprising the steps of:

a) immersing the object in a fluid;

b) arranging a plurality of ultrasonic transducers, each having a focal zone of a different depth relative to said object such that said plurality of transducers are positioned to focus ultrasonic beams from said transducers beginning at an exterior surface of the object and at successively increasing depths into the object, wherein a focal zone of each transducer partially overlaps a focal zone of each transducer focused at adjacent depths;

c) translating said plurality of ultrasonic transducers along the longitudinal axis of said object;

d) pulsing said ultrasonic transducers at a plurality of axially spaced-apart data positions to emit the ultrasonic beams at a uniform frequency throughout the entire volume of the object;

e) focusing the ultrasonic beams at progressively different depths throughout the object, the ultrasonic beams focused at the exterior surface of the object and focused successively in increasing depth within the object to form multiple prolate spherical focal zones oriented transversely to the longitudinal axis of the object, wherein a focal zone of each ultrasonic beam partially overlaps a focal zone of the ultrasonic beams focused at adjacent depths;

f) receiving echo signals from reflections of said ultrasonic beams from each of said plurality of transducers throughout the respective focal zones of the transducers at each of said plurality of data positions;

g) processing said echo signals to convert said signals into digital data in a format suitable for storing in a first readable memory medium;

h) further processing said digital data to generate an image of the object undergoing examination;

i) displaying said image of said object on a display means; and j) storing data representing said image of said object in a second readable memory medium.

2. A method as set forth in claim 1, further comprising the steps of:

k) rotating said object about said longitudinal axis;

l) pulsing said ultrasonic transducers a plurality of times at each of said plurality of axially spaced apart data positions as said object is rotated through a series of axial orientations to emit ultrasonic beams; and m) focusing the ultrasonic beams at progressively different depths throughout the object.

3. A method for non-destructively examining a cylindrical object comprising the steps of:

a) immersing the cylindrical object in a fluid;

b) arranging a plurality of ultrasonic transducers, each having a focal zone of a different depth relative to said cylindrical object such that said plurality of transducers are positioned to focus ultrasonic beams from said transducers beginning at an exterior surface of the cylindrical object and at successively increasing depths into the cylindrical object, wherein a focal zone of each transducer partially overlaps a focal zone of each transducer focused at adjacent depths;

c) initializing a data collector and processor to reference a first end of a longitudinal extent of said cylindrical object as a start point Z, and to reference a position on the circumference of the cylindrical object as a start point T;

d) rotating the cylindrical object;

e) translating said plurality of ultrasonic transducers along a longitudinal axis of said cylindrical object;

f) pulsing said ultrasonic transducers at a plurality of spaced-apart circumferential and longitudinal data positions to emit ultrasonic beams at a uniform frequency throughout the entire volume of the cylindrical object;

g) focusing the ultrasonic beams at progressively different depths throughout the cylindrical object, the ultrasonic beams focused at the exterior surface of the cylindrical object and focused successively in increasing depth within the cylindrical object to form multiple prolate spherical focal zones oriented transversely to the longitudinal axis of the cylindrical object, wherein a focal zone of each ultrasonic beam partially overlaps a focal zone of ultrasonic beams focused at adjacent depths;

h) receiving echo signals from reflections of said ultrasonic beams from each of said plurality of transducers throughout the respective focal zones of the transducers; and i) processing said echo signals to convert said signals into digital image data in a format suitable for storage in a predetermined memory medium.

4. Apparatus for nondestructively examining an object having an axial orientation comprising:

an immersion tank for receiving said object into an immersion fluid contained therein;

a plurality of ultrasonic transducers mounted to means for axially translating said transducers parallel to said axial orientation of said object, each successive one of said plurality of ultrasonic transducers having a focal zone at an increasing depth of said object, and wherein a portion of a focal zone of each transducer overlaps a portion of a focal zone of each adjacent transducer;

means coupled to each of said plurality of transducers for pulsing said transducers to emit ultrasonic beams at a uniform frequency throughout the entire volume of the object and for receiving signals back from said transducers generated by reflections of said ultrasonic beams;

means for focusing the ultrasonic beams at progressively different depths throughout the object, the ultrasonic beams focused at an exterior surface of the object and focused successively in increasing depth within the object to form multiple prolate spherical focal zones oriented transversely to an axis defining said axial orientation of the object, wherein a focal zone of each ultrasonic beam partially overlaps a focal zone of ultrasonic beams focused at adjacent depths;

means for rotating said object about the axis defining said axial orientation;

means for tracking an angular orientation of said object as said object is rotated;

means for generating an electrical signal indicative of said angular orientation of said object;

means for generating an electrical signal indicative of an axial position from each of said transducers;

means for converting said signals generated from said reflections of said ultrasonic beams to imaging data from which an image of said object can be generated;

means for generating said image of said object from said imaging data;

means for displaying said image; and memory means for storing said imaging data in digital form.

5. Apparatus as recited in claim 4, further comprising a graphical user interface operatively coupled to said means for displaying said image.

6. Apparatus as recited in claim 4, further comprising means for analyzing said imaging data, including means for selecting, on said display means, a region of interest.

7. Apparatus as recited in claim 6, wherein said selecting means comprises a graphical user interface.

8. Apparatus as recited in claim 7, wherein said imaging data analyzing means comprises a zoom feature to magnify a selected region of interest on said display means.

9. Apparatus as recited in claim 4, wherein said angular orientation tracking means and said angular orientation signal generating means comprise a rotary encoder operatively coupled to said image generating means.

10. A method as set forth in claim 1, wherein said displaying of said image of said object is a real-time display.

11. A method as set forth in claim 10, wherein said displaying of said image is done as a sliding window display, wherein a portion of the object being displayed is shifted as said plurality of transducers is translated along the longitudinal axis of the object.

12. A method as set forth in claim 2, wherein processing steps (g) and (h) are accomplished by a means for generating digital image data, and the method comprising the further step of:

n) providing to said means for generating digital image data a plurality of values of preselected parameters of the object to be examined, said parameters including an object diameter.

13. A method as set forth in claim 3, comprising the further step of:

j) displaying, in real time, said digital image data on a display means.

14. A method as set forth in claim 13, wherein said real-time display includes the further step of:

k) displaying said digital image data in a three-dimensional display format.

15. A method as set forth in claim 14, comprising the further step of:

l) analyzing said digital image data being displayed using a graphical user interface operatively coupled to said display.

* * * * *